United States Patent [19]

Evans et al.

[11] 4,088,773

[45] May 9, 1978

[54] ACYLAMINO DERIVATIVES

[75] Inventors: Delme Evans, Chalfont St. Peter; Michael Ralph John Jolley, Camberley; William James Ross, Lightwater; Brian Picton Swann, Camberley, all of England

[73] Assignee: Lilly Industries Limited, London, England

[21] Appl. No.: 691,964

[22] Filed: Jun. 1, 1976

[30] Foreign Application Priority Data

Jun. 5, 1975 United Kingdom ............... 24223/75

[51] Int. Cl.$^2$ .................... C07D 207/34; A61K 31/40
[52] U.S. Cl. ................................. 424/274; 260/326.2; 260/326.47; 260/326.5 R; 260/326.9
[58] Field of Search ..................... 260/326.2, 326.47; 424/274

[56] References Cited

U.S. PATENT DOCUMENTS

| | | | |
|---|---|---|---|
| 2,437,465 | 3/1948 | Goodings et al. | 260/326.47 |
| 2,785,181 | 3/1957 | Waller et al. | 260/326.47 |
| 2,901,489 | 8/1959 | Allen, Jr. et al. | 260/326.2 |
| 3,577,440 | 5/1971 | Leinsford et al. | 260/326.47 |
| 3,966,957 | 6/1976 | Cale, Jr. et al. | 424/274 |

FOREIGN PATENT DOCUMENTS 819,088   12/1974   Belgium ........................ 260/326.2

OTHER PUBLICATIONS

Herz et al.; Chem. Abs., vol. 52:352b (1956).

*Primary Examiner*—Donald G. Daus
*Assistant Examiner*—Mary C. Vaughn
*Attorney, Agent, or Firm*—Nancy J. Harrison; Everet F. Smith

[57] ABSTRACT

Acylamino pyrrole compounds having anti-allergic activity, methods of making the compounds and pharmaceutical formulations containing the compounds.

24 Claims, No Drawings

ACYLAMINO DERIVATIVES

This invention relates to heterocyclic chemical compounds and more particularly to certain novel 5-membered heterocyclics substituted by an acylamino group which possess utility in the treatment of immediate hypersensitivity conditions and/or which are useful as intermediates in preparing such active compounds. The invention also includes processes for preparing the compounds of the invention. Furthermore, the invention includes within its scope pharmaceutical compositions containing the pharmacologically active compounds and methods of treatment of animals, including humans, comprising administering thereto an effective dose of the compound or compounds or of pharmaceutical compositions comprising the active compound or compounds.

Certain acylamino pyrroles have been described in Belgian Patent Specification No. 819088. However, those known pyrroles are described as being intermediates or as having utilities, e.g. herbicidal, antiinflammatory, antipyretic, etc., quite divorced from the antiallergic activity which the novel compounds of the invention have been found to possess.

According to the present invention there is provided a novel pyrrole of formula (I):

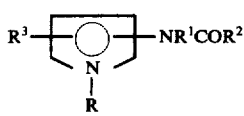
(I)

wherein R is hydrogen, $C_{1-6}$ alkyl or optionally substituted phenyl $C_{1-4}$ alkyl, $R^1$ is $C_{1-10}$ alkyl, $C_{3-6}$ alkenyl, $C_{3-6}$ alkynyl, $C_{2-6}$ alkoxyalkyl, $C_{2-6}$ carboxyalkyl, $C_{1-6}$ haloalkyl, $C_{3-10}$ cycloalkyl, $C_{3-10}$ cycloalkyl-$C_{1-6}$ alkyl, optionally substituted phenyl-$C_{1-6}$ alkyl or optionally substituted phenyl-$C_{2-6}$ alkenyl; and $R^2$ is $C_{1-8}$ alkyl, $C_{1-6}$ haloalkyl, $C_{2-6}$ alkenyl, $C_{3-10}$ cycloalkyl, $C_{3-10}$ cycloalkyl-$C_{1-6}$ alkyl, optionally substituted phenyl, optionally substituted phenyl-$C_{1-6}$ alkyl or optionally substituted phenyl-$C_{2-6}$ alkenyl; and wherein $R^3$ is hydrogen or $C_{1-4}$ alkyl.

The pyrrole nucleus may be substituted in any of the three available positions by a group selected from hydrogen and $C_{1-4}$ alkyl. By "available positions" there is meant any one of the three carbon atoms in the heteroaryl nucleus not substituted by the acylamino group —$NR^1COR^2$.

The acylamino group —$NR^1COR^2$ may be attached at the 2- or, preferably, the 3-position of the pyrrole nucleus.

The term "$C_{1-4}$ alkyl" as used herein means a straight or branched chain alkyl group containing from 1 to 4 carbon atoms, namely methyl, ethyl, isopropyl, n-propyl, n-butyl, isobutyl, s-butyl, t-butyl. "$C_{1-4}$ hydroxyalkyl" and "$C_{3-6}$ acyloxyalkyl" mean the aforementioned $C_{1-4}$ alkyl groups substituted with an hydroxy group and acyloxy group respectively. "$C_{2-6}$ alkoxyalkyl" and "$C_{1-6}$ haloalkyl" mean the aforementioned $C_{1-6}$ alkyl groups substituted with an alkoxy group or one or more halogen atoms, such as methoxyethyl, ethoxyethyl, ethoxybutyl, dibromomethyl, trifluoromethyl, 1-chloroethyl, 1,1-dichloroethyl, 1-iodobutyl or pentafluoroethyl.

The terms "$C_{2-6}$ alkynyl" and "$C_{3-6}$ alkynyl" are used herein to indicate alicyclic hydrocarbon groups having 2 to 6 and 3 to 6 carbon atoms which contain a —C≡C— group. However, it should be noted that the —C≡C— group cannot be directly adjacent the nitrogen atom of the acylamino group, similarly a —C≡C— group cannot be directly adjacent said nitrogen atom in a $C_{3-6}$ alkenyl group.

"$C_{3-10}$ cycloalkyl" means a saturated ring having from 3 to 10 carbon atoms in the ring such as cyclopropyl, cyclobutyl, cyclopentyl, cyclooctyl, or adamantyl.

The term "optionally substituted phenyl" as used herein means a phenyl group unsubstituted or substituted by one or more groups which do not substantially alter the pharmacological activity of the compounds of formula I, such as halogen, trifluoromethyl, methyl, methoxy, or nitro groups. The term "optionally substituted phenyl $C_{1-4}$ alkyl" refers to phenyl substituted by the aforementioned groups and joined to the adjacent nitrogen atom by a $C_{1-4}$ alkylene bridge.

The term "$C_{2-6}$ carboxyalkyl" as used herein means a $C_{1-5}$ alkyl group substituted by a carboxylic acid group. Examples of such groups are carboxymethyl, carboxyethyl, carboxypropyl and carboxybutyl.

Preferred classes of compounds falling within the scope of the heterocyclic derivatives of formula (I) above are those having one or more of the following characteristics:

(A) R is $C_{1-3}$ alkyl,
(B) R is methyl,
(C) $R^1$ is $C_{1-7}$ alkyl, $C_{3-6}$ alkenyl, $C_{3-6}$ alkynyl or benzyl optionally substituted by halogen or nitro,
(D) $R^1$ is $C_{2-6}$ alkyl, $C_{3-6}$ alkenyl or benzyl optionally substituted by halogen,
(E) $R^1$ is $C_{3-6}$ alkyl, $C_{3-4}$ alkenyl or benzyl,
(F) $R^2$ is $C_{1-7}$ alkyl, $C_{3-10}$ cycloalkyl, phenyl or benzyl,
(G) $R^2$ is $C_{1-7}$ alkyl, $C_{3-5}$ cycloalkyl or phenyl,
(H) $R^2$ is $C_{1-4}$ alkyl,
(I) $R^2$ is $C_{1-4}$ alkyl, $C_{3-5}$ cycloalkyl, or phenyl,
(J) $R^3$ is hydrogen,
(K) the acylamino group —$NR^1COR^2$ is present at the 2- or 3-position of the pyrrole nucleus and $R^3$ is a $C_{1-4}$ alkyl substituent at the 5-position,
(L) $R^3$ is methyl.

The compounds of formula (I) may be prepared by alkylating an acyl derivative of formula:

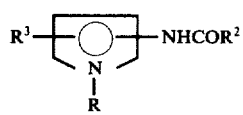
(IX)

where R, $R^2$ and $R^3$ are as defined above.

Compounds of formula (IX) can be alkylated by dissolving the amide in a suitable inert, anhydrous, polar solvent such as dimethylformamide, forming an alkali metal salt thereof with an alkali metal hydride, preferably sodium hydride, and then treating the salt with an alkylating agent of formula $R^1X$ where X is a reactive atom such as a halogen atom, preferably iodine, or a reactive group such as an alkyl sulphate group.

Of course, alkylating agents and alkylating reaction conditions other than those specified above can be utilised, the nature of these being readily apparent to those acquainted with the art.

Pyrroles of formula:

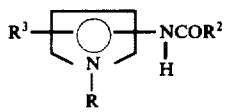

can be prepared by the simultaneous reduction and acylation of the corresponding nitro derivatives of formula:

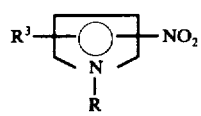

This simultaneous reduction and acylation can be carried out using hydrogen over platinum oxide in the presence of an acylating agent such as the appropriate acid anhydride.

Intermediates of formula (IX) except when R is methyl, $R^2$ is methyl and $R^3$ is hydrogen are novel, and are provided in a further aspect of the invention.

Compounds of formula (I) have been shown to be useful in the prophylactic and therapeutic treatment of immediate hypersensitivity diseases including asthma and in the alleviation of *status asthmaticus*. The compounds have low toxicity.

The compound or compositions of the present invention may be administered by various routes and for this purpose may be formulated in a variety of forms. Thus the compounds or compositions may be administered by the oral and rectal routes, topically, parenterally, e.g. by injection and by continuous or discontinuous intra-arterial infusion, in the form of, for example, tablets, lozenges, sub-lingual tablets, sachets, cachets, elixirs, suspensions, aerosols, ointments, for example, containing from 1 to 10% by weight of the active compound in a suitable base, soft and hard gelatin capsules, suppositories, injection solutions and suspensions in physiologically acceptable media, and sterile packaged powders adsorbed onto a support material for making injection solutions. Advantageously for this purpose, compositions may be provided in dosage unit form, preferably each dosage unit containing from 5 to 500 mg. (from 5.0 to 50 mg. in the case of parenteral administration, from 5.0 to 50 mg. in the case of inhalation and from 25 to 500 mg. in the case of oral or rectal administration) of a compound of formula (I). Dosages of from 0.5 to 300 mg/kg per day, preferably 0.5 to 20 mg/kg of active ingredient may be administered although it will, of course, readily be understood that the amount of the compound or compounds of formula (I) actually to be administered will be determined by a physician, in the light of all the relevant circumstances including the condition to be treated, the choice of compound to be administered and the choice of route of administration and therefore the above preferred dosage range is not intended to limit the scope of the present invention in any way.

In this specification, the expression "dosage unit form" is used as meaning a physically discrete unit containing an individual quantity of the active ingredient, generally in admixture with a pharmaceutical diluent therefor, or otherwise in association with a pharmaceutical carrier, the quantity of the active ingredient being such that one or more units are normally required for a single therapeutic administration or that, in the case of severable units such as scored tablets, at least one fraction such as a half or a quarter of a severable unit is required for a single therapeutic administration.

The formulations of the present invention normally will consist of at least one compound of formula (I) mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semi-solid or liquid material, which serves as a vehicle, excipient or medium for the active therapeutic substance.

Some examples of the diluents or carriers which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup B.P., methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tabletting machine. For such purpose there may be employed for instance aluminium, magnesium or calcium stearates, talc or mineral oil.

The invention will now be further illustrated by reference to the following Examples.

EXAMPLE 1

N-(1-Methylpyrrol-2-yl)acetamide

1-Methyl-2-nitropyrrole (15.0 g, 0.1189 mol) in acetic anhydride (60 ml) and triethylamine (150 ml) was hydrogenated over platinum oxide (1.50 g) at room temperature and pressure. The reaction was halted when 3.3 equivalents of hydrogen had been taken up. The catalyst was filtered off and the filtrate evaporated in vacuo to leave a dark oil (18.1 g). This was chromatographed on a silica column using 10% ethyl acetate/ether as solvent to give a clear oil (8.7 g) which discoloured rapidly on exposure to light and/or air. This was then distilled under vacuum to give a colourless oil (7.20 g) (44%). b.p. (airbath) 130° C/0.15 mm. The mass spectrum showed a mass ion at 138 and infrared and proton magnetic resonance spectra also supported the structure.

EXAMPLE 2

2-Methyl-N-(1-methylpyrrol-2-yl)propanamide

The title compound (m.p. 122°–4° C) was prepared using a similar method to that described in Example 1.

EXAMPLE 3

N-Butyl-N-(1-methylpyrrol-2-yl)acetamide

N-(1-Methylpyrrol-2-yl)acetamide (3.20 g, 0.0231 mol) in dry dimethylformamide was maintained at a temperature less than 0° C, with stirring under nitrogen, during the slow addition of 50% sodium hydride/oil (1.11 g, 0.0231 mol). After the addition, the mixture was stirred at 0° C. for 30 minutes and then the temperature allowed to rise to 15° C. when n-butyl iodide (8.50 g, 0.0461 mol) was added. The mixture was stirred at room temperature overnight and then poured into water (200 ml) and the mixture extracted with ether (4 × 50 ml). The combined extracts were washed with water (3 × 50 ml) and dried over magnesium sulphate. The solvent was removed in vacuo and the resulting oil distilled to give a colourless oil 3.72 g (83%) b.p. (airbath) 100° C/0.4 mm.

Analysis: $C_{11}H_{18}N_2O$ req.: C 68.0; H 9.3; N 14.4; O 8.2%: found: C 67.7; H 9.6; N 14.25; O 8.0%.

EXAMPLES 4 and 5

Similarly prepared were N-(1-Methylpyrrol-2-yl)-N-(2-propenyl)acetamide, b.p. (airbath) 100° C/0.4 mm.

Analysis: $C_{10}H_{14}N_2O$ req.: C 67.4; H 7.9; N 15.7; O 9.0%: found: C 67.2; H 7.9; N 15.8; O 9.0%.

and N-Butyl-2-methyl-N-(1-methylpyrrol-2-yl)propanamide, b.p. (airbath) 110° C/0.6 mm.

EXAMPLE 6

2-Methyl-N-(1-methylpyrrol-3-yl)propanamide

1-Methyl-3-nitropyrrole (30.40 g, 0.2410 mol) in 2-methylpropanoic anhydride (200 ml) and triethylamine (340 ml) was hydrogenated over platinum oxide (3.0 g) at 60 p.s.i. and room temperature. The uptake of hydrogen was theoretical. The catalyst was removed by filtration and the filtrate evaporated in vacuo to give a dark oil, which was dissolved in ethyl acetate and washed with 15% aq. sodium carbonate, and then with water. The organic phase was then dried and evaporated in vacuo. The resulting fawn solid was recrystallised from ethyl acetate/carbon tetrachloride to give colourless needles (17.13 g) (43%), m.p. 125°-125.5° C.

Analysis: $C_9H_{14}N_2O$ req.: C 65.0; H 8.5; N 16.85; O 9.6%: found: C 65.1; H 8.3; N 16.7; O 9.9%.

EXAMPLE 7

Similarly prepared was N-(1-Methylpyrrol-3-yl)acetamide (m.p. 120°-120.5° C).

EXAMPLE 8

N,2-Dimethyl-N-(1-Methylpyrrol-3-yl)propanamide

2-Methyl-N-(1-methylpyrrol-3-yl)propanamide (2.50 g, 0.015 mol) in dry dimethylformamide (10 ml) was cooled to below 0° C. and stirred under nitrogen during the addition of 50% sodium hydride/oil (0.73 g, 0.0152 mol). After the addition, the mixture was stirred at 0° C. for 30 minutes and then brought to 15° C. when iodomethane (4.30 g, 0.0302 mol) was added. The mixture was stirred at room temperature overnight and then poured into water (200 ml) and the mixture extracted with ether (4 × 50 ml). The combined extracts were washed with water (3 × 50 ml) and dried over magnesium sulphate. The solvent was removed in vacuo to leave a solid which separated from pentane at −10° C as white flakes (2.11 g, 78%).

Analysis: $C_{10}H_{16}N_2O$ req.: C 6.66; H 8.95; N 15.5%: found: C 66.35; H 8.7; N 15.6%.

EXAMPLES 9 to 16

Similarly prepared were:

2-Methyl-N-(1-methylpyrrol-3-yl)-N-(2-propenyl)-propanamide (m.p. 54°-54.5° C).

Analysis: $C_{12}H_{18}N_2O$ req.: C 69.9; H 8.8; N 13.6; O 7.8%: found: C 69.7; H 8.7; N 13.5; O 7.5%.

N-Butyl-2-methyl-N-(1-methylpyrrol-3-yl)-propanamide (m.p. 57°-57.5° C.).

Analysis: $C_{13}H_{22}N_2O$ req.: C 70.2; H 10.0; N 12.6; O 7.2%: found: C 70.15; H 9.7; N 12.6; O 7.5%.

N-Hexyl-2-methyl-N-(1-methylpyrrol-3-yl)-propanamide (m.p. 31°-31.5° C).

Analysis: $C_{15}H_{26}N_2O$ req.: C 71.95; H 10.5; N 11.2; O 6.4%: found: C 71.7; H 10.3; N 11.1; O 6.65%.

2-Methyl-N-(1-methylpyrrol-3-yl)-N-(phenylmethyl)propanamide (m.p. 73°-74° C).

Analysis: $C_{16}H_{20}N_2O$ req.: C 75.0; H 7.9; N 10.9; O 6.2%: found: C 74.7; H 7.55; N 11.2; O 6.4%.

2-Methyl-N-(1-methylpyrrol-3-yl)-N-(4-bromophenylmethyl)propanamide (m.p. 88°-89° C).

Analysis: $C_{16}H_{19}BrN_2O$ req.: C 57.3; H 5.7; Br 23.8; N 8.4; O 4.8%: found: C 57.1; H 5.7; Br 23.6; N 8.1; O 4.75%.

N-(1-Methylpyrrol-3-yl)-N-(2-propenyl)-acetamide (b.p. (airbath) 120° C/0.4 mm).

Analysis: $C_{10}H_{14}N_2O$ req.: C 67.4; H 7.9; N 15.7; O 9.0%: found: C 67.4; H 8.0; N 15.6; O 9.1%.

N-Butyl-N-(1-methylpyrrol-3-yl)-acetamide (b.p. (airbath) 110° C/0.5 mm).

Analysis: $C_{11}H_{18}N_2O$ req.: C 68.0; H 9.3; N 14.4; O 8.2%: found: C 67.75; H 9.3; N 14.25; O 8.5%.

N-(1-Methylpyrrol-3-yl)-N-(phenylmethyl)-acetamide (b.p. (airbath) 150° C/0.4 mm).

Analysis: $C_{14}H_{16}N_2O$ req.: C 73.7; H 7.0; N 12.3; O 7.0%: found: C 73.4; H 7.0; N 12.3; O 7.3%.

EXAMPLES 18 to 21

Similarly, using the methods described in Examples 1 to 8, with appropriate modification of starting materials, the following compounds can be prepared.

N-Hexyl-2-methyl-N-(1,4-dimethylpyrrol-3-yl)-propanamide.

N-Hexyl-2-methyl-N-(1,5-dimethylpyrrol-3-yl)-propanamide.

N-n-Propyl-2-methyl-N-(1-methyl-4-i-propylpyrrol-3-yl)-propanamide.

N-Hexyl-2-methyl-N-(1-i-propylpyrrol-3-yl)-propanamide.

The following Examples 22 to 26 illustrate pharmaceutical formulations containing the active compound N-(1-methylpyrrol-3-yl)-N-(phenylmethyl)acetamide.

EXAMPLE 22

Soft gelatin capsules were prepared using the following ingredients:

| | Quantity (mg/capsule) |
|---|---|
| Active compound | 30 |
| Propyl gallate | 0.02 |
| Fractionated Coconut Oil B.P.C. | 70 |
| | 100.02 |

The above ingredients were mixed and filled into soft gelatin capsules, the main shell components of which were gelatin and glycerine.

EXAMPLE 23

Hard gelatin capsules were prepared using the following ingredients:

| | Quantity (mg/capsule) |
|---|---|
| Active compound | 30 |
| Silicon dioxide (fumed) | 25 |

7

-continued

| | Quantity (mg/capsule) |
|---|---|
| Lactose | 45 |
| Butylated hydroxyanisole B.P. | 0.02 |

The butylated hydroxyanisole was dissolved in the active ingredient and the solution so formed adsorbed onto the silicon dioxide (fumed). The lactose was then added and the whole mixed. Finally, the mixture was filled into hard gelatin capsules.

EXAMPLE 24

Suppositories containing 30 and 60 mg. of the compound are prepared as follows:

| Active compound | 3 g. |
|---|---|
| Henkel base | 97 g. |

The active compound is mixed with the Henkel base which had been previously melted using the minimum amount of heat possible. The mixture is then poured into suppository moulds of a nominal capacity of 1 g, or 2 g, as desired, to produce suppositories each containing 30 mg. or 60 mg. of the active compound.

EXAMPLE 25

An aerosol was prepared containing the following ingredients:

| | Quantity per ml. |
|---|---|
| Active compound | 15 mg. |
| Propylene glycol | 15 mg. |
| Dichlorotetrafluoroethane (Propellant 114) | 600 mg. |
| Dichlorodifluoromethane (Propellant 12) | 850 mg. |

The active compound is mixed with the propylene glycol and the mix added to the propellant 114, the mixture cooled to −15° to −20° C. and transferred to a filling device. At the same time a mixture of propellants 114 and 12, previously cooled to −15° to −20° C. is fed into a second filling device. A metered amount of propellant from the second filling device is introduced into a stainless steel container, followed by the required amount of material from the first filling device. The valve units are then fitted and sealed to the container. These valve units may be equipped with metering device so that approximately 0.20 mg. of the active compound is released by a single actuation of the valve.

EXAMPLE 26

Tablets were prepared using the following components:

| Active compound | 15.00 | mg. |
|---|---|---|
| Microcrystalline Cellulose | 250.00 | mg. |
| Sodium Carboxymethyl Starch | 20.00 | mg. |
| Magnesium Stearate | 3.00 | mg. |
| Butylated Hydroxyanisole B.P. | 0.002 | mg. |

The hydroxyanisole was dissolved in the active compound, the solution adsorbed onto the microcrystalline cellulose. This was mixed with the sodium carboxymethyl starch and then the magnesium stearate was mixed in. Finally, the mixture was compressed to form tablets.

8

In the foregoing Examples 22 to 26 the liquid active compound used may, in accordance with the invention, be replaced wholly or in part by other liquid active compounds of formula (I). If the active compound is a solid, appropriate modification will of course have to be made.

We claim:

1. A pyrrole of the formula

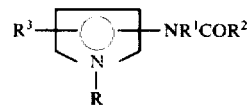

wherein R is hydrogen, $C_{1-6}$ alkyl, phenyl $C_{1-4}$ alkyl, or phenyl $C_{1-4}$ alkyl wherein the phenyl group is mono substituted with halogen, trifluoromethyl, methyl, methoxy, or nitro; $R^1$ is $C_{1-10}$ alkyl, $C_{3-6}$ alkenyl, $C_{3-6}$ alkynyl, $C_{2-6}$ alkoxyalkyl, $C_{2-6}$ carboxyalkyl, $C_{1-6}$ haloalkyl, $C_{3-10}$ cycloalkyl, $C_{3-10}$ cycloalkyl-$C_{1-6}$ alkyl, phenyl-$C_{1-6}$ alkyl, phenyl-$C_{2-6}$ alkenyl, or phenyl-$C_{1-6}$ alkyl and phenyl-$C_{2-6}$ alkenyl wherein the phenyl group is mono substituted with halogen, trifluoromethyl, methyl, methoxy and nitro; and $R^2$ is $C_{1-8}$ alkyl, $C_{1-6}$ haloalkyl, $C_{2-6}$ alkenyl, $C_{3-10}$ cycloalkyl, $C_{3-10}$ cycloalkyl-$C_{1-6}$ alkyl, phenyl, phenyl-$C_{1-6}$ alkyl, phenyl-$C_{2-6}$ alkenyl, or phenyl, phenyl-$C_{1-6}$ alkyl and phenyl-$C_{2-6}$ alkenyl wherein the phenyl group is mono substituted with halogen, trifluoromethyl, methyl, methoxy, and nitro; and $R^3$ is hydrogen or $C_{1-4}$ alkyl.

2. A pyrrole of claim 1 having the formula:

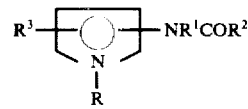

wherein R is $C_{1-4}$ alkyl, $R^1$ is $C_{1-7}$ alkyl, $C_{3-6}$ alkenyl, benzyl, or benzyl substituted by a halogen atom, $R^2$ is $C_{1-4}$ alkyl and $R^3$ is hydrogen or $C_{1-4}$ alkyl.

3. A pyrrole according to claim 2, wherein $R^1$ is $C_{2-6}$ alkyl, $C_{3-6}$ alkenyl, benzyl, or benzyl substituted by halogen and $R^3$ is hydrogen.

4. The pyrrole according to claim 2 which is N-(1-methylpyrrol-3-yl)-N-(phenylmethyl)-acetamide.

5. A pyrrole of claim 2 wherein the —$NR^1COR^2$ substituent is located at the 3-position of the pyrrole nucleus.

6. The compound of claim 2 which is N-butyl-N-(1-methylpyrrol-2-yl)acetamide.

7. The compound of claim 2 which is N-(1-methylpyrrol-2-yl)-N-(2-propenyl)acetamide.

8. The compound of claim 2 which is N-butyl-2-methyl-N-(1-methylpyrrol-2-yl)propanamide.

9. The compound of claim 2 which is N,2-dimethyl-N-(1-methylpyrrol-3-yl)propanamide.

10. The compound of claim 2 which is 2-methyl-N-(1-methylpyrrol-3-yl)-N-(2-propenyl)propanamide.

11. The compound of claim 2 which is N-butyl-2-methyl-N-(1-methylpyrrol-3-yl)propanamide.

12. The compound of claim 2 which is N-hexyl-2-methyl-N-(1-methylpyrrol-3-yl)propanamide.

13. The compound of claim 2 which is 2-methyl-N-(1-methylpyrrol-3-yl)-N-(phenylmethyl)propanamide.

14. The compound of claim 2 which is 2-methyl-N-(1-methylpyrrol-3-yl)-N-(4-bromophenylmethyl)propanamide.

15. The compound of claim 2 which is N-(1-methylpyrrol-3-yl)-N-(2-propenyl)acetamide.

16. The compound of claim 2 which is N-butyl-N-(1-methylpyrrol-3-yl)acetamide.

17. The compound of claim 2 which is N-hexyl-2-methyl-N-(1,4-dimethylpyrrol-3-yl)propanamide.

18. The compound of claim 2 which is N-hexyl-2-methyl-N-(1,5-dimethylpyrrol-3-yl)propanamide.

19. The compound of claim 2 which is N-n-propyl-2-methyl-N-(1-methyl-4-i-propylpyrrol-3-yl)propanamide.

20. The compound of claim 2 which is N-hexyl-2-methyl-N-(1-i-propylpyrrol-3-yl)propanamide.

21. A pharmaceutical formulation useful for the treatment of asthma containing a chemotherapeutically-effective amount of a pyrrole of the formula

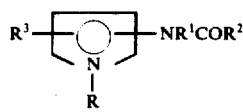

wherein R is hydrogen, $C_{1-6}$ alkyl, phenyl $C_{1-4}$ alkyl or phenyl $C_{1-4}$ alkyl wherein the phenyl is mono substituted with halogen, trifluoromethyl, methyl, methoxy, and nitro; $R^1$ is $C_{1-10}$ alkyl, $C_{3-6}$ alkenyl, $C_{3-6}$ alkynyl, $C_{2-6}$ alkoxyalkyl, $C_{2-6}$ carboxyalkyl, $C_{1-6}$ haloalkyl, $C_{3-10}$ cycloalkyl, $C_{3-10}$ cycloalkyl-$C_{1-6}$ alkyl, phenyl-$C_{1-6}$ alkyl, phenyl-$C_{2-6}$ alkenyl, or phenyl-$C_{1-6}$ alkyl and phenyl-$C_{2-6}$ alkenyl wherein the phenyl group is mono substituted with halogen, trifluoromethyl, methyl, methoxy and nitro; $R^2$ is $C_{1-8}$ alkyl, $C_{1-6}$ haloalkyl, $C_{2-6}$ alkenyl, $C_{3-10}$ cycloalkyl, $C_{3-10}$ cycloalkyl-$C_{1-6}$ alkyl, phenyl, phenyl-$C_{1-6}$ alkyl, phenyl-$C_{2-6}$ alkenyl, or phenyl, phenyl-$C_{1-6}$ alkyl and phenyl-$C_{2-6}$ alkenyl wherein the phenyl group is mono substituted with halogen, trifluoromethyl, methyl, methoxy and nitro; and $R^3$ is hydrogen or $C_{1-4}$ alkyl, in association with a pharmaceutically-acceptable carrier therefor.

22. A pharmaceutical formulation of claim 21 containing as active ingredient a chemotherapeutically effective amount of a pyrrole of the formula:

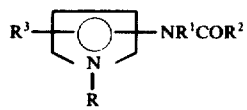

wherein R is $C_{1-4}$ alkyl, $R^1$ is $C_{1-7}$ alkyl, $C_{3-6}$ alkenyl, benzyl, or benzyl substituted by a halogen atom, $R^2$ is $C_{1-4}$ alkyl and $R^3$ is hydrogen or $C_{1-4}$ alkyl; associated with a pharmaceutically acceptable carrier therefor.

23. A method of treating an animal suffering from, or susceptible to, asthma which comprises administering to the animal a chemotherapeutically-effective amount of a pyrrole of the formula

wherein R is hydrogen, $C_{1-6}$ alkyl, phenyl $C_{1-4}$ alkyl or phenyl $C_{1-4}$ alkyl wherein the phenyl is mono substituted with halogen, trifluoromethyl, methyl, methoxy, and nitro; $R^1$ is $C_{1-10}$ alkyl, $C_{3-6}$ alkenyl, $C_{3-6}$ alkynyl, $C_{2-6}$ alkoxyalkyl, $C_{2-6}$ carboxyalkyl, $C_{1-6}$ haloalkyl, $C_{3-10}$ cycloalkyl, $C_{3-10}$ cycloalkyl-$C_{1-6}$ alkyl, phenyl-$C_{1-6}$ alkyl, phenyl-$C_{2-6}$ alkenyl, or phenyl-$C_{1-6}$ alkyl and phenyl-$C_{2-6}$ alkenyl wherein the phenyl group is mono substituted with halogen, trifluoromethyl, methyl, methoxy, and nitro; $R^2$ is $C_{1-8}$ alkyl, $C_{1-6}$ haloalkyl, $C_{2-6}$ alkenyl, $C_{3-10}$ cycloalkyl, $C_{3-10}$ cycloalkyl-$C_{1-6}$ alkyl, phenyl, phenyl-$C_{1-6}$ alkyl, phenyl-$C_{2-6}$ alkenyl, or phenyl, phenyl-$C_{1-6}$ alkyl and phenyl-$C_{2-6}$ alkenyl wherein the phenyl group is mono substituted with halogen, trifluoromethyl, methyl, methoxy and nitro; and $R^3$ is hydrogen or $C_{1-4}$ alkyl.

24. A method of claim 23 which comprises administering to the animal a chemotherapeutically effective amount of a pyrrole of the formula:

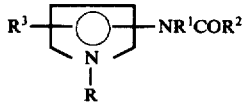

wherein R is $C_{1-4}$ alkyl, $R^1$ is $C_{1-7}$ alkyl, $C_{3-6}$ alkenyl, benzyl, or benzyl substituted by a halogen atom, $R^2$ is $C_{1-4}$ alkyl and $R^3$ is hydrogen or $C_{1-4}$ alkyl.

* * * * *